United States Patent [19]

Talish et al.

[11] Patent Number: 4,574,809

[45] Date of Patent: Mar. 11, 1986

[54] PORTABLE NON-INVASIVE ELECTROMAGNETIC THERAPY EQUIPMENT

[75] Inventors: Roger J. Talish, Fairfield; William E. Parr, Denville; Steven J. Zavros, Morristown, all of N.J.

[73] Assignee: Electro-Biology, Inc., Fairfield, N.J.

[21] Appl. No.: 626,340

[22] Filed: Jun. 29, 1984

[51] Int. Cl.$^4$ ............................................. A61N 1/40
[52] U.S. Cl. ................................. 128/419 F; 128/1.5
[58] Field of Search ............... 128/1.5, 419 F, 419 R, 128/421 PS, 422, 423 R, 804

[56] References Cited

U.S. PATENT DOCUMENTS

| | | | |
|---|---|---|---|
| 2,764,683 | 9/1956 | Paust et al. | 128/423 R |
| 3,902,502 | 9/1975 | Liss et al. | 128/422 |
| 3,942,535 | 3/1976 | Schulman | 128/419 PS |
| 4,197,851 | 4/1980 | Fellus | 128/422 |
| 4,266,533 | 5/1981 | Ryaby et al. | 128/421 |
| 4,456,001 | 6/1984 | Pescatore | 128/419 F |
| 4,459,988 | 7/1984 | Dugot | 128/419 F |

FOREIGN PATENT DOCUMENTS 1267046 3/1972 United Kingdom ......... 128/419 PS

*Primary Examiner*—William E. Kamm
*Attorney, Agent, or Firm*—Hopgood, Calimafde, Kalil, Blaustein & Judlowe

[57] ABSTRACT

The invention contemplates a cast-embedable coil structure which includes a single connector fitting, designed for exposure externally of a completed cast and for removable mounting and electrical connection to a self-contained light-weight rechargeable portable signal-generator unit. The signal-generator unit is mounted to the cast only for periods of therapeutic treatment, and it is removably mounted to a less-portable charging unit in intervals between periods of therapeutic treatment. The same connector fitting on the generator unit (a) establishes all necessary electrical connections for therapy when mounted to the cast fitting and (b) establishes all necessary electrical connections for recharging when mounted to the charging unit. Various automatic and display functions are provided in the signal-generator unit and in the charging unit.

16 Claims, 5 Drawing Figures

PORTABLE NON-INVASIVE ELECTROMAGNETIC THERAPY EQUIPMENT

BACKGROUND OF THE INVENTION

This invention relates to the treatment of living tissues and/or cells by altering their interaction with charged species in their environment. More particularly, the invention relates to an electromagnetic body-treatment device for surgically non-invasive modification of the growth, repair and maintenance behavior of living tissues and cells by a specific and selective change in electrical environment.

Ryaby, et al., U.S. Pat. Nos. 4,105,017, 4,266,532 and 4,266,533 describe means for effecting surgically non-invasive direct inductive coupling to an afflicted body region, whereby one or more electric voltage and concomitant current signals conform to a highly specific pattern and have been found to develop therapeutically beneficial treatment of the affcted region, as for example in the enhancement of repair of bone fractures, nonunions, and the like. In general, the involved treatment head or heads have involved one or more large coils, which have served well for the treatment of large-member bones, as in leg regions. And various special-purpose coil and head configurations have been disclosed for specific treatments. In general, it may be said that it has been preferred practice to employ a treatment-head configuration in which two like coils are electrically connected in flux-aiding relation and have flexibly articulated connection to enable strapped application on opposite sides of an afflicted limb, and with the coils on a common axis of magnetic-flux development through the afflicted region. However, for certain injuries, such as bone injury in the carpal-navicular region of the arm, it becomes very awkward, bothersome, and inconvenient to use the conventional articulated-coil technique, in that use of the arm must be severely curtailed, due primarily to treatment-head considerations. It is also a source of considerable inconvenience, during treatments, to limit the patient to plugged-in electrical connection to a desk or otherwise mounted signal generator.

Pending U.S. application Ser. No. 473,801, filed Mar. 9, 1983 begins to address the problem of the patient's personal inconvenience, by disclosing expendable single-use coil structures of light weight and bulk, intended for embedment in a conventional cast and with removable plug-in connection to the pulse-signal generator, the generator being in accordance with said Ryaby, et al. patents. The patient is not encumbered by coil bulk outside his cast, but his connection to a desk or table-mounted generator unit is required for each therapeutic treatment.

BRIEF STATEMENT OF THE INVENTION

It is an object of the invention to provide a new approach to treatment-head and pulse-generator design in equipment of the character indicated, with a view to total portability in the course of periods of therapeutic treatment.

It is a specific object to provide an improved treatment-head component, particularly suited to integration with an orthopedic cast and particularly suited to removable assembly with a portable signal generator, for periods of therapeutic treatment.

Another specific object is to provide a self-contained portable signal generator having removable adaptability to a treatment head of the character indicated.

A further specific object is to meet the above objects with a portable signal generator which is additionally removably adaptable to a desk or table-mounted charging unit in intervals between periods of therapeutic treatment.

It is also a specific object to meet the foregoing specific objects with a portable signal generator wherein the same connector removably mounts the signal generator to the treatment head or to the charging unit, wherein such connections are by way of the same simple connection procedure, wherein connection to the treatment head automatically initiates a treatment, and wherein connection to the charging unit automatically initiates a charging operation.

A general object is to achieve the above objects with structure of elemental simplicity and low cost, and featuring minimum modification of conventional orthopedic casting technique.

The invention achieves the foregoing objects with a cast-embedable coil structure which includes a single connector fitting, designed for exposure externally of a completed cast and for removable mounting and electrical connection to a self-contained light-weight rechargeable portable signal-generator unit. The signal-generator unit is mounted to the cast only for periods of therapeutic treatment, and it is removably mounted to a less-portable charging unit in intervals between periods of therapeutic treatment. The same connector fitting on the generator unit (a) establishes all necessary electrical connections for therapy when mounted to the cast fitting and (b) establishes all necessary electrical connections for recharging when mounted to the charging unit. Various automatic and display functions are provided in the signal-generator unit and in the charging unit.

DETAILED DESCRIPTION

The invention will be illustratively described for a preferred embodiment, in conjunction with the accompanying drawings, in which.

Figure 1:
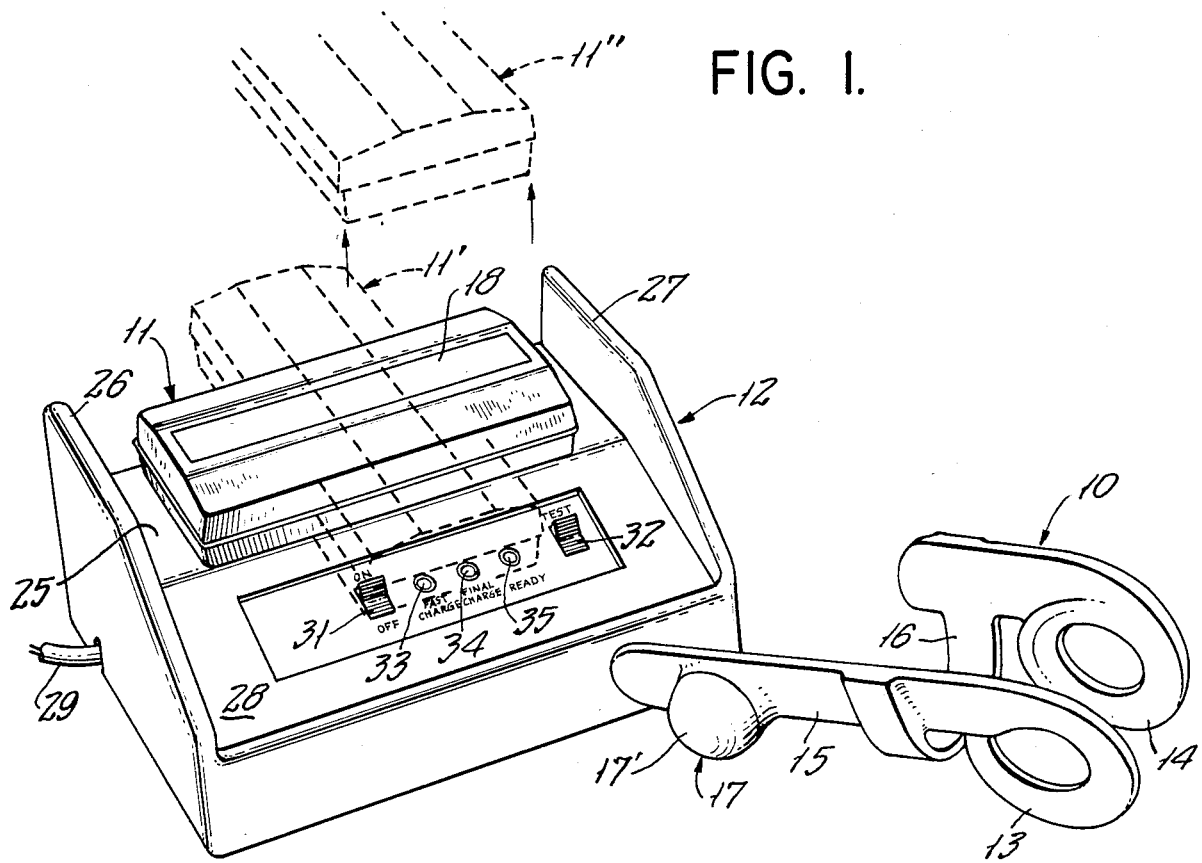
FIG. 1 is a perspective view of three component units involved in use of the invention, one of the units being an electrical coil assembly adapted for embedment in or enclosure within an orthopedic cast.

Three units of FIG. 1 comprise a coil unit 10, a pulse-generator unit 11, and a charging unit 12. The coil unit 10 may be of various sizes and configurations depending upon the body region to be treated but is shown to be of the general nature described in said copending application Ser. No. 473,801, being adapted for treatment of fractures in the carpal-navicular region. Specifically, unit 10 comprises like multi-turn electrical coils contained within spaced annuli 13–14 of pliable magnetically transparent plastic having integral connection to a relatively stiffly pliant elongate base or arm 15; the coil of annulus 13 is united to one end or arm 15 and the coil of annulus 14 is united to arm 15 via a semicylindrical pliant strap connection or bridge 16, both members 15–16 being also magnetically transparent. Electrical leads to the coils within annuli 13–14 will be understood to be encased in plastic within bridge 16 and arm 15 and to be interconnected for flux-aiding excitation via a single connector fitting 17, the latter being securely mounted to base arm 15 and at substantial longitudinal offset from the space defined by and between the coils of annuli 13–14. In FIG. 1, a removable cap 17' is shown protecting electrical-lead contacts within connector 17, until such time as containment and fixing within an orthopedic cast has been completed.

Figure 3:
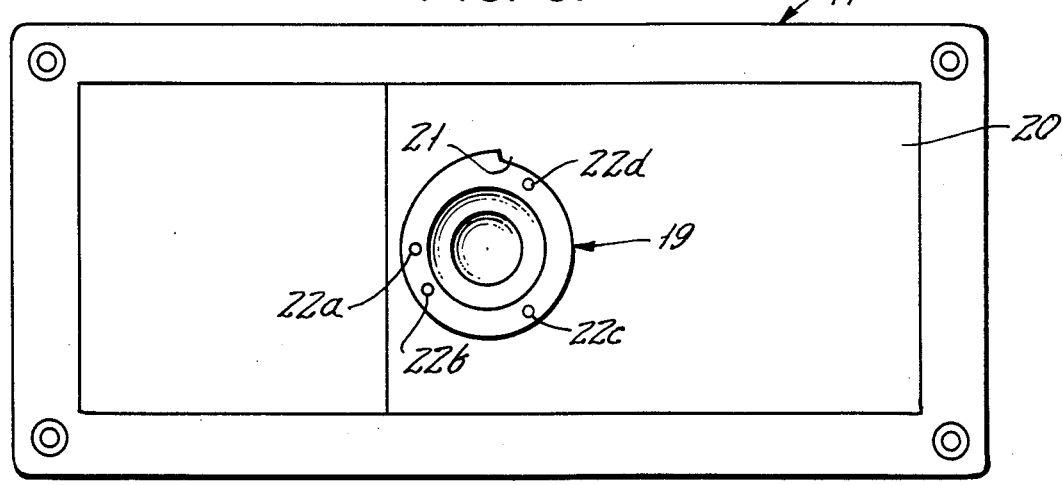
FIG. 3 is a view of the underside of another of the units of FIG. 1, on an enlarged scale.

The pulse-generator unit 11 will be understood to include a self-contained rechargeable battery and electronic means for generating pulse signals as described in said Ryaby, et al. patents. Unit 11 is shown as a relatively thin light-weight elongate rectangular box having visual-display means beneath a window 18 on its upper surface, and a single connector fitting 19 centrally exposed on its lower surface 20 (see FIG. 3). The connector fitting 19 of unit 11 and the connector fitting 17 of unit 10 are detachably fitted to each other via an axial insertion, followed by partial rotation, to complete a bayonet-locking engagement, wherein a lug (not shown) of fitting 17 engages under an arcuate rim 21 of the fitting 19, and upon completion of a quarter turn about the axis of connector engagement four exposed electrical contacts 22a,b,c,d of the signal-generator unit 11 will be understood to have made electrical contact with corresponding spaced contacts in fitting 17, all as will be more fully explained in connection with FIG. 5.

The desk or otherwise mountable charging unit 12 is shown to be generally rectangular and to provide a horizontal deck region 25 between spaced upstanding side panels 26–27, and a control panel 28 slopes downwardly from deck region 25 to the front of the unit; and a flexible cable 29 provides for local electrical-supply connection. Controls shown on panel 28 include an ON/OFF switch 31, a TEST switch 32, and lamps 33, 34, 35 indicative of fast-charge, final-charge, and ready conditions of the battery in unit 11.

A connector fitting (not shown) similar to the fitting 17 of unit 10 will be understood to be centrally mounted and upwardly exposed in the deck region 25, for electrically charging interconnection with contacts 22 of the generator unit 11, when in the charging position shown in solid-line outline in FIG. 1. The thus-connected relation of units 11 and 12 will be understood also to involve a bayonet-locking engagement which is completed (and which completes all electrical connections between units 11–12) when the elongate dimension of unit 11 registers with the elongate deck dimension between side panels 26–27. The vertical and horizontal dimensions of panels 26–27 will be seen to overlap the projected-end areas of unit 11 when in charging position, thus protecting the same against accidental dislodgement from charging position.

FIG. 1 further shows that, to remove the charged pulse-generator unit 11 for connection to a coil-head unit 10, the housing of unit 11 must be first partially rotated, as to the dashed-line position 11', whereupon it is axially removed by upward lifting, suggested by arrows associated with another dashed outline 11".

Figure 2:
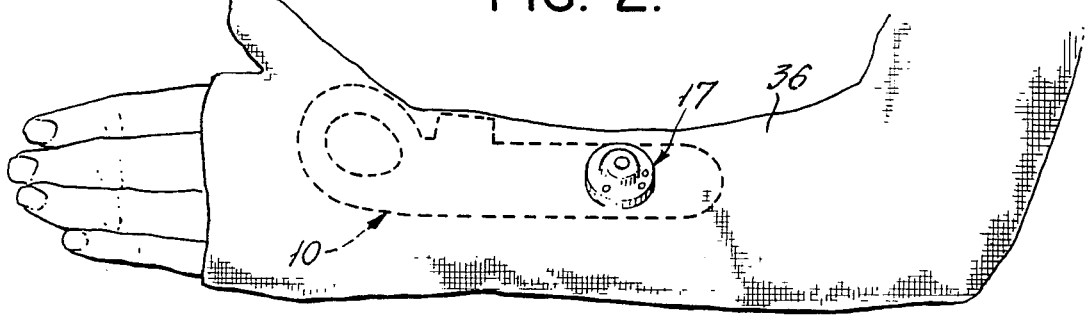
FIG. 2 is a view in elevation of a patient's arm fitted with an orthopedic cast containing the coil assembly of FIG. 1.

FIG. 2 illustrates application of the coil unit 10 to the treatment of a scaphoid-bone fracture in the arm of a patient, the unit 10 being embedded or otherwise contained within an orthopedic cast 36 of the long-arm variety, with external exposure of the connector fitting 17, following removal of its protective cap 17', so as to expose the angularly spaced electrical contacts of fitting 17. More specifically, it is recommended that the arm be prepared for casting in the usual manner, using a wrap of stockinette and padding, with allowance for a thumb spica, and with the wrist in neutral position. A thin layer of casting material is then applied, omitting thumb coverage, and the thickness of the cast at the scaphoid is measured, to assure a thickness consistent with specified spacing of coil annuli 13–14. After the cast has set, the treatment-coil unit 10 should be adhesively taped (e.g., at arm 15, between locations of bridge 16 connection and connector 17) to the cast, with the coil window over the scaphoid fracture, i.e., with the scaphoid fracture contained within the geometrical volume defined by and between openings of the respective coil annuli, and with the connector fitting 17 positioned over the dorsal radial aspect of the forearm. An X-ray viewing of the wrist is then recommended, in the dorsal/volar plane, to confirm the correctness of coil placement; the fracture should be clearly visible within the coil window, and a true A/P X-ray of the coils is necessary to confirm proper coil positioning. The cast is then completed, over the arm and coil unit 10, leaving the connector cap 17' exposed, the thumb spica being incorporated in the process, care being taken not to allow casting material above the bottom edge of the connector fitting 17. And cap 17' can be removed after the cast has set.

Figure 4:
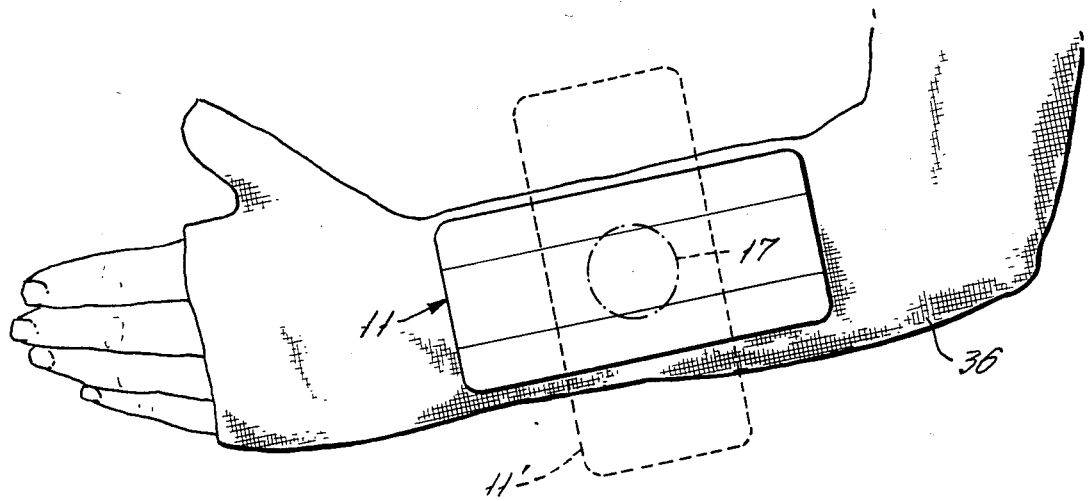
FIG. 4 is a view similar to FIG. 2, to show assembly of the unit of FIG. 3 thereto.

FIG. 4 shows that the charged pulse-generator unit 11, after removal from charging unit 12, is assembled to the exposed connector 17 of the cast by initial orientation transverse to the forearm (see dashed outline 11'), followed by axial engagement of fittings 17–19, and then a quarter-turn displacement to complete the bayonet engagement and to immediately commence delivery of excitation signals to the coils of unit 10. Treatment continues for a prescribed period of time, after which a quarter-turn twist of unit 11 effects its disconnection, and it should be reapplied to the charging unit 12 so as to be in readiness for the next period of treatment.

Figure 5:
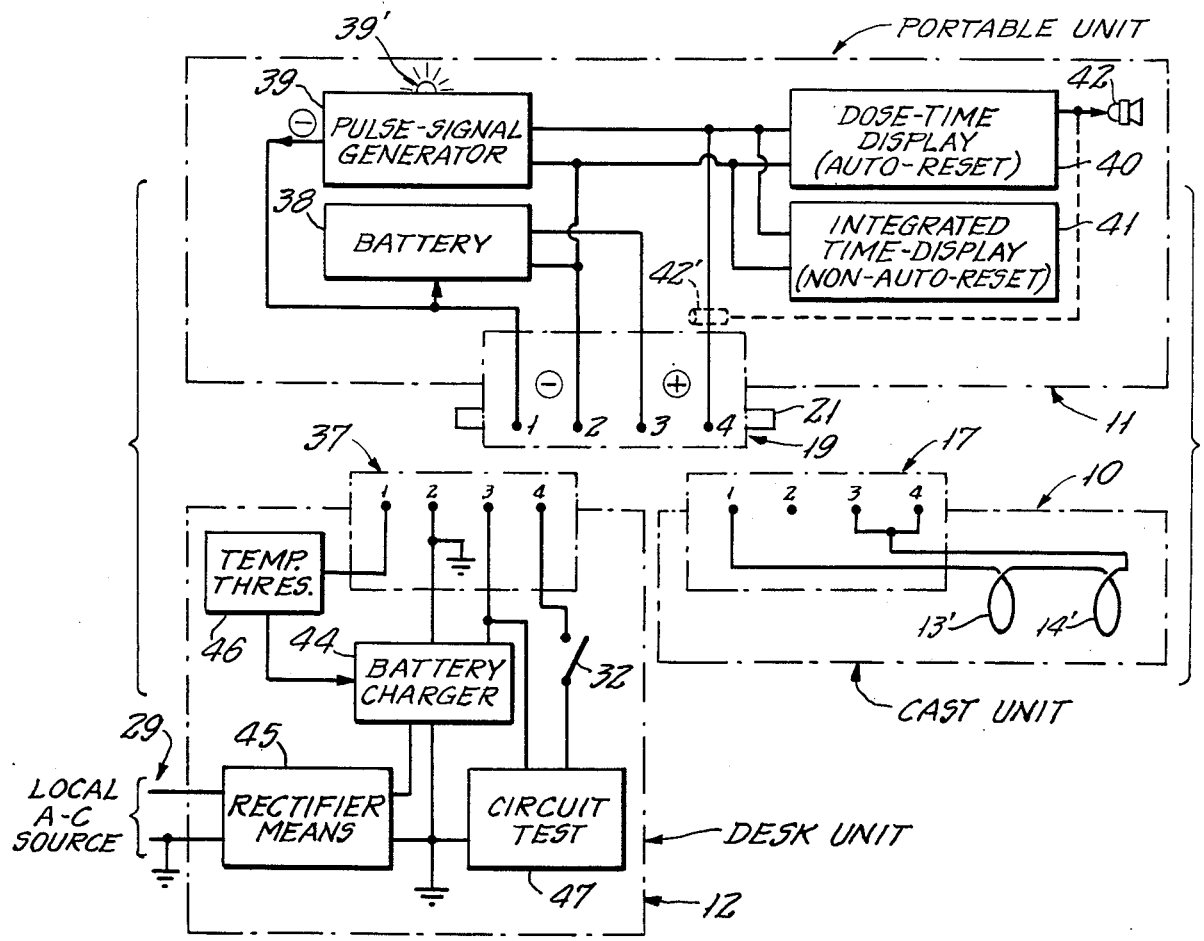
FIG. 5 is an electrical block diagram schematically showing components and detachable electrical connections, for all three of the units of FIG. 1.

In the block diagram of FIG. 5, basic electrical connections are depicted for all three of the units 10–11–12, via their connector fittings 17–19–37, respectively. Each of these fittings 17–19–37 is shown with four contacts, designated 1-2-3-4 in each case in order to show the matching of contact numbers when particular connectors 17 and 19 (or 19 and 37) are in engaged position.

The portable generator unit 11 is seen to include a rechargeable battery 38 and a pulse-signal generator 39, as well as a clock with dose-time display 40 (with automatic reset, as at each disconnect of fittings 17–19) and an integrated-time display 41 (without automatic reset) to record total hours of use. An audible alarm device 42 sounds upon expiration of each prescribed dose time.

Within the cast unit 10, the two coils 13–14' within annuli 13–14 are shown connected in series, with one lead connected to contact 1 of connector 17, with no connection to contact 2, and with the other coil lead connected to both contacts 3 and 4.

The charging unit 12 is shown to include a charging circuit 44 served by rectifier means 45, and the output of the charging circuit is connected across contacts 2 and 3 of connector 37, contact 2 being grounded. The contact-1 position is allocated to a temperature-sensing voltage which responds to temperature in battery 38 when fitting 19-37 of units 11-12 are connected; such temperature sensing will be understood to reflect charged status of the battery 38 and to be evaluated by a temperature-threshold circuit 46, in such controlling relation with the charging circuit 44 as to automatically reduce the charging rate upon achievement of the threshold voltage which reflects the predetermined battery temperature at which charging rate should be reduced, and indicator lamps at 33-34—35 will be understood to display the instantaneous charging or charged condition of unit 11. At fitting 37, contact 4 of unit 12 is allocated to a circuit-test function at 47, namely for testing the output of pulse generator 39 when units 11-12 are connected.

The electrical operations will be briefly reviewed, first for charging (units 11-12 and their fittings 19-37 connected) and then for pulsed excitation of the cast unit 10 (units 10-11 and their fittings 17-19 connected). When units 11-12 are connected, direct battery-charger output is made, via contacts 2 and 3 of fittings 19-37, to the rechargeable battery, and the rate of charging depends on temperature-tracking voltage (via contacts 1 and 2 of fittings 19-37). Also, circuit-testing of the pulse-signal generator 39 is available at key 32 (via contacts 1 and 4 of fittings 19-37).

Upon removal of the portable unit 11 from charging unit 12, it is important to note that the output of battery 38 is open-circuit and that there is no drain on the battery until portable unit 11 is assembled to the cast unit 10. The fact of such assembly causes a circuit to the pulse generator 39 to be completed via the bridge connection between contacts 3 and 4 of the cast-unit fitting 17. Thereafter, the pulsed-signal output of generator 39 is delivered to coils 13'-14', via connected contacts 1 and 4 of the fittings 17-19. This action continues, with accompanying clock and eventual alarm functions at 40-41-42, and until separation of the portable unit 11 from the cast unit; alternatively, it will be understood that the connection to alarm 42 is symbolic of a variety of functions which may signal the end of a prescribed dose, as for example an automatic relay-operated disconnection of the battery 38 from the pulse generator, the latter being suggested by dashed-line symbolism 42'.

The described invention will be seen to achieve all stated objects. Limitations on the patient are substantially reduced, and there are no technical burdens imposed by his merely operating the bayonet-locking connections for treatment and for charging, as the case may be. If the pulse generator 39 includes an indicator lamp 39' (viewable at window 18) and responding only to peak pulse output of at least predetermined sufficient amplitude, then the patient can always know whether his generator 39 output is adequate or if his battery 38 needs replacement or recharging, battery replacement being via a removable panel 48 (FIG. 3) on the underside of portable unit 11.

While the invention has been described in detail for a preferred form, it will be understood that modifications may be made without departing from the scope of the invention. For example, the showing in application to coils specifically adapted for schaphoid-bone treatment is not limiting in that other coil configurations designed for treatment of other parts of the body may be supplied with like facility, via a removably connected signal-generator unit 10. Thus, for a coil configuration embedded in a leg cast for treatment of a tibia or fibular fracture, for example within a long-leg cast having an exposed connector fitting 17, the location of fitting 17 may be selected to permit inconspicuous attachment of portable unit 11, as at a location where it can be concealed within a trouser leg or other clothing.

Although two or more of units 10-11-12 may be viewed as a kit, in view of their adaptability for use in combination as disclosed herein, it will be understood that each of these units is a separate article of commerce, and that the units 11-12 may be repeatedly reused in conjunction with successive expendable coil units 10 or the like, as the latter may have been dedicated to the individual bone-injury or defect situations of a variety of different patients.

What is claimed is:

1. Electromagnetic body-treatment apparatus for surgically non-invasive modification of the growth, repair and maintenance behavior of living tissues and cells by a specific and selective change in electrical environment, comprising a unitary coil insert for an orthopedic cast or the like, said insert including in interconnecting relationship a multiturn electrical coil and a combined electrical and mechanical connector fitting, said insert being embedable in such cast or the like with said connector fitting exposed; a self-contained portable signal-generator unit containing a rechargeable battery, said signal-generator unit having a complemental fitting for selective mating attachment to said connector fitting for simultaneously establishing structurally supportive mounting of said signal-generator unit on said coil insert and electrical connection thereto, and said signal-generator unit including a signal generator connected to said battery for supplying electrical-excitation pulse signals to said multiturn coil when said complemental fitting is attached to said connector fitting; and a charging unit having a mating fitting complemental to said complemental fitting for selective mating attachment to said complemental fitting of said signal-generator unit for simultaneously establishing structurally supportive mounting of said signal-generator unit on said charging unit and electrical connection thereto, said charging unit operating to supply electrical charging-current to said battery when said complemental fitting and said mating fitting are attached.

2. Electromagnetic body-treatment apparatus for surgically non-invasive modification of the growth, repair and maintenance behavior of living tissues and cells by a specific and selective change in electrical environment, comprising a unitary coil insert for an orthopedic cast or the like, said insert including in interconnecting relationship a multiturn electrical coil and a combined electrical and mechanical connector fitting, said insert embedable in such cast or the like with said connector fitting exposed; and a self-contained portable signal-generator unit containing a rechargeable battery, said signal-generator unit having a complemental fitting for selective mating attachment to said connector fitting for simultaneously establishing structurally supportive mounting of said signal-generator unit on said coil insert and electrical connection thereto, and said signal-generator unit including a signal generator connected to said battery for supplying electrical-excitation pulse signals to said multiturn coil when said complemental fitting is attached to said connector fitting.

3. The apparatus of claim 2 in which said fittings comprise telescopically axially engageable relatively rotatable members with interengaging lug means operative to lock said members against axial separation upon a fractional relative rotation thereof when in fully axially engaged relation.

4. The apparatus of claim 3, in which said fittings include plural electrical contact means at different locations about the axis of relative rotation, said contact means being angularly positioned to establish electrical connection of the output of said signal-generator means to said electrical coil only upon fractional relative rotation to the locked condition of said members.

5. The apparatus of claim 4, including in combination a charging unit having a mating fitting complemental to said complemental fitting for selective mating attachment to said complemental fitting of said signal-generator unit, said mating fitting of said charging unit having a member that is axially engageable and relatively rotatable with respect to the fitting member of said signal-generator unit with interengaging lug means operative to lock said signal-generator unit to said charging unit upon a fractional relative rotation thereof when in fully axially engaged relation.

6. The apparatus of claim 7, in which said fittings of said signal-generator unit and of said charging unit include plural electrical contact means at different offsets from the axis of relative rotation, said last-mentioned contact means being angularly positioned to establish electrical charging connection of the output of said charging unit to said battery only upon fractional relative rotation to the locked condition of said charging unit and said signal-generator unit.

7. The apparatus of claim 6, in which said charging unit includes means responsive to the charged condition of said battery for reducing the charging rate upon sensed existence of a predetermined first level of battery charge.

8. The apparatus of claim 6, in which said charging unit includes means responsive to sensed achievement of a fully charged condition of said battery for reducing the output of said charging unit to a trickle-charge modality.

9. The apparatus of claim 4, in which the connection of said battery to said signal generator is via said contact means, whereby neither said signal generator nor said coil is energized in the absence of locked engagement of said signal-generator unit to said coil insert.

10. The apparatus of claim 9, in which said contact means includes a bridge connection of two contacts of said connector fitting of said coil insert, and in which circuit connection of said battery to said signal generator includes two contacts which rely on conduction via said two contacts of said connector fitting.

11. The apparatus of claim 4, in which said signal-generator unit includes a clock with an externally viewable time display, and means responsive to achievement of a locked engagement of said signal-generator unit to said coil insert for activating said clock only for the time duration of said locked engagement.

12. The apparatus of claim 4, in which said signal-generator unit includes a clock timer of predetermined dosage, and automatic means responsive to completion of a predetermined dosage.

13. The apparatus of claim 12, in which said automatic means includes means producing an audible signal of the completed-dose.

14. The apparatus of claim 12, in which said automatic means includes means operative to disconnect said battery from said signal generator upon completion of the predetermined dosage.

15. The apparatus of claim 2, in which said coil insert comprises a stiffly flexible elongate strip of magnetically transparent material, and in which said coil is a single multiturn electrical coil of initially generally circular configuration and fixed to one side of said strip, with said strip extending in at least one radially outward direction from said coil and to and including an offset location of mounting said connector fitting.

16. The apparatus of claim 15, in which said coil is one of two like coils, and in which a stiffly flexible strip of magnetically transparent material is so connected to said first-mentioned strip and to the second of said coils as to position said coils on opposite sides of an afflicted region with the axes of said coils in at least approximate alignment, said last-defined strip having arched local conformance to body-surface curvature between the opposite body sides served by said coils.

* * * * *